United States Patent
Tipton

[11] 3,973,554
[45] Aug. 10, 1976

[54] RADIATION SAFETY SHIELD FOR A SYRINGE

[75] Inventor: Harold W. Tipton, Woodbridge, Va.

[73] Assignee: The United States of America as represented by the Secretary of the Department of Health, Education and Welfare, Washington, D.C.

[22] Filed: Apr. 24, 1975

[21] Appl. No.: 571,214

[52] U.S. Cl. ............................... 128/1.1; 128/2 A; 128/215; 250/506
[51] Int. Cl.² ............................................ A61B 6/00
[58] Field of Search .......... 128/2 A, 1.1, 1.2, 218 F, 128/218 P, 215; 250/506

[56] References Cited
UNITED STATES PATENTS

| | | | |
|---|---|---|---|
| 3,655,985 | 4/1972 | Brown et al. | 250/506 X |
| 3,673,411 | 6/1972 | Glasser | 250/506 |
| 3,769,490 | 10/1973 | Czaplinski | 250/506 X |
| 3,814,941 | 6/1974 | Czaplinski | 128/1.1 X |
| 3,820,541 | 6/1974 | Langan | 128/1.1 X |
| 3,863,623 | 2/1975 | Trueblood et al. | 128/2 A |

*Primary Examiner*—Kyle L. Howell
*Attorney, Agent, or Firm*—Browdy and Neimark

[57] ABSTRACT

A safety apparatus for use in administering radioactive serums by a syringe, without endangering the health and safety of the medical operators, consists of a sheath and a shield which can be retracted into the sheath to assay the radioactive serum in an assay well. The shield can be moved from the retracted position into an extended position when the serum is to be injected into the patient. To protect the operator, the shield can be constructed of tantalum or any like high density substance to attenuate the radiation, emanating from the radioactive serums contained in the syringe, from passing to the atmosphere. A lead glass window is provided so that the operator can determine the exact quantity of the radioactive serum which is contained in the syringe.

8 Claims, 3 Drawing Figures

RADIATION SAFETY SHIELD FOR A SYRINGE

FIELD OF THE INVENTION

This invention relates to syringes and has particular utility in protecting an operator from undue exposure to repeated doses of radiation emanating from a radioactive serum contained in the syringe.

BACKGROUND OF THE INVENTION

In recent years, medical researchers have made substantial break-throughs in combating and treating a number of serious disorders. Many of these advances have come in the field of chemotherapy whereby chemicals are administered to a patient to treat or diagnose a disease without having an unduly adverse effect on the patient. This technique is used in the field of cancer therapy whereby different chemicals are introduced into the body of the patient in order to inhibit the spread of the disease or to detect a diseased area. Many of these chemical agents contain highly radioactive isotopes or serums and while the dosages applied are themselves not lethal, constant and repeated contacts with the serums over an extended period of time can create very harmful effects on the medical technicians and operators who administer them.

While several radiation safety shields are in use at the present time, none of these shields adequately protects the technician and at the same time allows him to precisely assay the amount of radioactive material that is injected into the patient. A lead shield which only affords limited protection to the operator is presently in routine use. After a syringe is placed in the shield of this device and the serum withdrawn, the syringe must be removed to assay the serum. This exposes the clinical personnel to unnecessary and harmful radiation. Also, due to its bulk, the device makes an injection quite difficult to administer.

A patented device relates to a shield for a hypodermic syringe adapted to surround the barrel of the syringe to protect the user against radiation emanating from radioactive fluids contained therein. This shield is lead lined, and is provided with a bayonet-fitting element engaging the manually held end of the syringe. A coil spring cooperates with the bayonet-fitting element to prevent wobbling between the barrel of the syringe and the barrel of the shield. The barrel of the shield is so configured that a small end of the barrel of the syringe is uncovered to permit visual inspection of flow, to and from the syringe. However, as can easily be seen, this shield can neither be retracted to allow an assay of the serum in a satisfactory manner, nor does the device contain a means to ensure that a proper dosage is introduced into the syringe.

SUMMARY OF THE INVENTION

It is, accordingly, an object of the present invention to overcome the defects of the prior art as mentioned above.

Another object of the present invention is to provide a radiation safety shield for a syringe which can safely, easily and conveniently be used by medical technicians.

A further object of the present invention is to provide a radiation safety shield which can be retracted when the syringe is lowered into an assay well, and then can be returned to its original position when the syringe is removed from the well.

Still another object of the present invention is to supply a radiation safety shield which can be used in conjunction with a standard syringe.

Yet another object of the present invention is to provide a radiation safety shield which contains a lead glass window to ensure that a proper dosage is introduced into the syringe.

Another object is to improve safety and convenience in the administration of radioactive substances.

Another object of the present invention is to supply a radiation safety shield which contains a locking mechanism locking the shield in a retracted position when the radioactive substance is assayed.

These and other objects of the invention are fulfilled by using with a syringe, a removably cooperating retractable shield which eliminates any unnecessary exposure to the radioactive substance contained in the syringe. With the shield in place, a high density metal such as tantalum attenuates the radiation to a safe level. When the operator wishes to assay the radioactive material contained in the syringe, he merely retracts the shield as the filled syringe is lowered into the assay well. After the completion of the assay, the shield is moved over the exposed part of the syringe to prevent radiation leakage and thereby render any radiation levels safe to the operator. Injection of the radioactive substance is now possible and easily accomplished because the shield configuration closely resembles that of the syringe. A locking mechanism is included in the shield for holding the syringe in place. The shield also contains a lead glass window to ensure that a proper dosage is withdrawn into the syringe.

BRIEF DESCRIPTION OF THE DRAWING

The above and additional objects and advantages of the present invention will become more apparent by reference to the description of an illustrated embodiment in a drawing thereof in which.

DETAILED DESCRIPTION OF A PREFERRED EMBODIMENT

Figure 1:
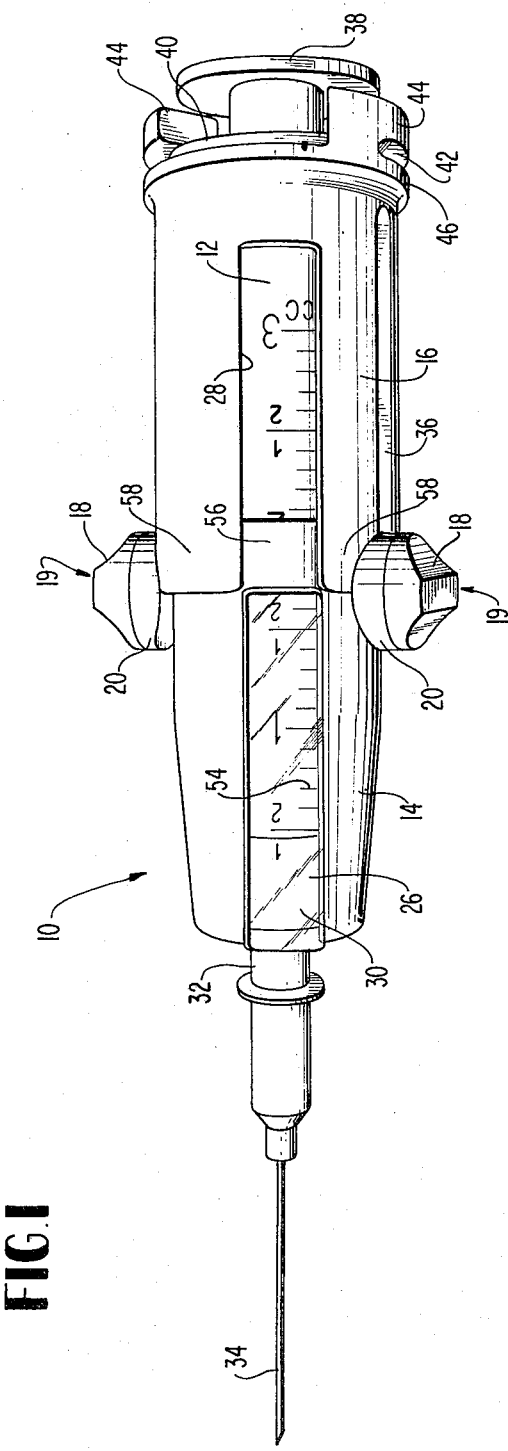
FIG. 1 is a side view of the radiation retraction shield and a syringe inserted therein.

FIG. 1 shows a radiation safety shield assembly 10 which is in its unretracted position and which contains a standard syringe 12 containing a needle 34 and embossed with calibrations 54 to indicate the quantity of dosage contained therein. Any conventional plastic type syringe may be used with the safety shield assembly 10, it being appreciated that the dimensions of each separate shield assembly can be changed according to the dimensions of the particular syringe which is utilized.

The assembly contains a substantially retractable shield 14 which is machined from a high density metal such as tantalum or lead capable of attenuating significant amounts of radiation and which is movable within a substantially cylindrical sheath 16. The shield 14 is the main protective entity in this device and therefore must be made of a very high density material so as to protect the users from any radioactive substances contained in the syringe 12.

In order to enable the operator to precisely know the exact dosage which is contained within the syringe 12, a lead glass window 26 is provided on the shield 14. This window 26 can be affixed to the shield 14 in any conventional manner such as by epoxy resin or other suitable glue. The sheath 16 has an aperture 28 contained on its surface but since the function of this sheath is not to protect the user from the harmful effects of radiation, the aperture can be left completely open.

It should be noted that the upper portion of shield assembly (the sheath 16) need not be constructed of high density material, but may be constructed of any lightweight conventional material (e.g., plastic or metal) since, in operation, the syringe is filled to a level not greater than the limits of the shield 14. For example, in the assembly as depicted in FIG. 1, the syringe 12 is shown to contain only a ½ cc dosage of radioactive serum 30. Thus to ensure the safety of the medical technicians, the syringe should not be filled beyond the limits of the shield 14. The serums which are used in conjunction with the safety shield assembly do not radiate outwardly in a manner such that radiation rays would "turn the corner" beyond the shield end 56. For example, a 1 cc dosage of Technetium -99m which can expose the operator to radiation levels as high as 800 mr/min during assay, was found to be attenuated down to an acceptable level of 3.0 mr/min utilizing the present device.

Figure 3:
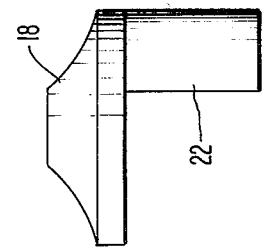
FIG. 3 is a view of the slide button of the radiation safety shield.
Figure 2:
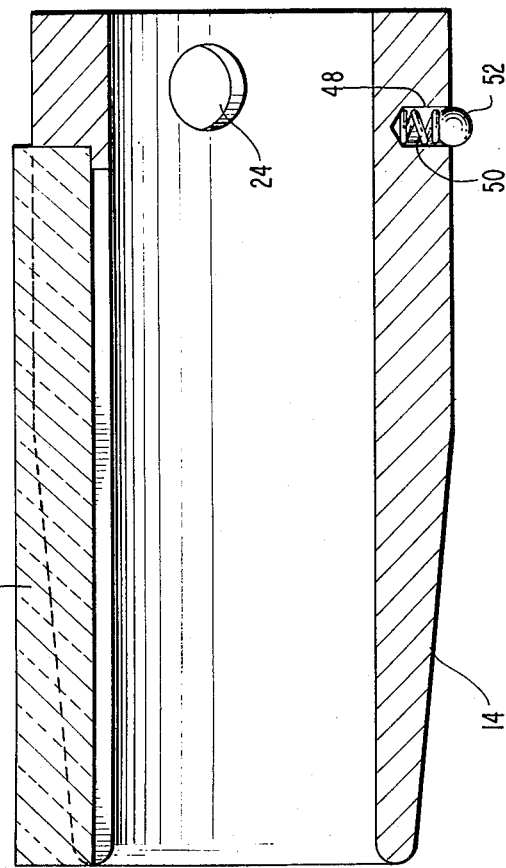
FIG. 2 is a side view cross-section of the radiation safety shield.

To ensure that the syringe 12 is kept in place, the sheath 16 contains two locking mechanisms 19 each of which is composed of a slide button 18 and a washer-like bushing 20. The slide button 18 can be composed of any material similar to that of the sheath 16 and the bushing 20 can be composed of a solid slippery material, e.g. acetal resin such as Delrin. Each slide button 18 (see FIG. 3) contains a male plug 22 which is retained within an opening 24 in the shield 14. The bushing 20 has a central hole through which the plug 22 extends to mate the bushing 20 with the slide button 18, and the locking mechanism 19 is then press-fitted into the shield 14 by the interconnection of the plug 22 in the hole 24. The sheath 16 is provided with two oppositely spaced elongated slots or runways 36, each associated with one of the locking mechanisms 19, in each case the sheath 16 being interposed between the bushing 20 and the shield 14 with the plug passing freely through the runway 36. This configuration allows for the smooth retraction or telescoping of the shield 14 within the sheath 16 as well as holding the shield 14 in any intermediate position between full retraction and full extension.

The end of the sheath 16 furthermost from the syringe needle 34 has also been designed to hold the syringe 12 firmly in place. An annular flange 46 which circles the entire circumference of the sheath end is provided to interact with two sheath appendages 44 which are separated from the annular flange 46 by an annular groove 42. This groove is adapted to receive a syringe flange 40 contained on the distal end 38 of the syringe 12.

To ensure that the shield 14 remains in a retracted position when the serum is assayed, a compression spring housing 48 is drilled or otherwise provided in the shield 14 so as to receive a compression spring 50 and a ball 52 in such a manner that the compression spring 50 forces the ball 52 outward from the compression spring housing 48. When the shield 14 is fully extended and protection is at its optimal level, the ball 52 extends into a recess (not shown) on the inner surface of the sheath 16 at its proximal end 58. Another recess (not shown) is contained in the distal end of the sheath 16 so that when the shield 14 is fully retracted, it will be held firmly in place by the action of the ball 52 in this recess, and may be released by a small pushing action on the slide button 18.

The above described safety shield can be operated in the following manner. The syringe 12 is inserted into the shield assembly when the shield 14 is retracted within the sheath 16. The locking mechanisms 19 are enabled to travel along the outer edge of the sheath 16 when the shield 14 is retracted due to the two runways 36, spaced 180° from one another on the outer sheath circumference. A twisting motion will lock the syringe in place. The shield 14 is then moved forward over the exposed end of the syringe at which point the ball 52 will enter the recess of the proximal end of the sheath. The serum is then withdrawn into the syringe 12, care being taken that the syringe is not filled more than the length of the shield 14.

In order to determine the exact radioactivity of the serum which is being utilized, the syringe 12 is then lowered into an assay well and the shield is again retracted to allow for the radiation count. As it is removed from the assay well, the shield 14 is returned over the exposed end of the syringe, and the device is then ready for patient injection. As previously stated, any conventional syringe may be utilized in conjunction with the shield assembly. This syringe contains a colorless hub 32 which helps the technician in determining whether any of the radioactive substance was being withdrawn or injected into the patient.

While this device has been described with particular reference to the serum Technetium-99m, it should not be construed to be so limited and may be utilized with many other radioactive serums. It will be obvious to those skilled in the art that various changes may be made without departing from the scope of the invention and the invention is not to be construed as limited to what is shown in the drawings and described in the specification.

What is claimed is:

1. A radiation safety apparatus for use with a syringe for containing a radioactive liquid, comprising:
   a cylindrical sheath for encircling the distal end of a syringe;
   a retractable cylindrical shield for encircling the proximal end of the syringe and constructed of a material capable of attenuating significant amounts of radiation from a radioactive source, said shield being coaxial with said sheath and being capable of retracting into said sheath; and
   means to couple said shield and said sheath coaxially together and to permit said shield to telescope into said sheath while being frictionally maintained in axial position relative to said sheath;
   wherein said shield is extensible over the proximal end of the syringe to ensure that radioactive rays do not escape when the syringe contains a radioactive serum, but whereby said shield can be retracted within said sheath to allow for assaying of a radioactive substance.

2. A radiation safety apparatus according to claim 1, further including a locking means for locking said shield in a retracted position when the radioactive substance is assayed.

3. A radiation safety shield according to claim 2, wherein said locking mechanism includes a ball and compression spring.

4. A radiation safety shield according to claim 1 wherein said means to couple said shield and sheath comprises a pair of guideways in said sheath, a pair of plugs extending from said shield each passing through one of said guideways, and a slidable member mounted on each plug in slidable relation with the outer surface of said sheath.

5. A radiation safety apparatus according to claim 1, further including a lead glass window in said shield in order to be able to ascertain the amount of radioactive substance contained in the syringe.

6. A radiation safety apparatus according to claim 1 wherein said shield is constructed of tantalum or lead.

7. A radiation safety apparatus for use with a syringe comprising:
- a cylindrical sheath for encircling the distal end of a syringe;
- a retractable cylindrical shield for encircling the proximal end of the syringe and constructed of a material capable of attenuating significant amounts of radiation from a radioactive source, said shield being coaxial with and being slidably connected to said sheath to allow said shield to be retracted into said sheath;
- locking means for locking said shield in a retracted position when the radioactive substance is assayed, said locking means comprising a pair of guideways in said sheath, a pair of plugs extending from said sheath each passing through one of said guideways, and a slidable member mounted on each plug in slidable relation with the outer surface of said sheath;
- wherein when a radioactive serum is drawn into the syringe, the radioactive rays are shielded by said shield and do not pass through the atmosphere, but said shield can be retracted within said sheath to allow for assaying of the radioactive substance.

8. A method for assaying radioactive serums in a syringe before injecting serum into a patient comprising the steps of:
- inserting a syringe into a radiation safety apparatus having a shield and sheath with said shield covering the proximal end of the syringe;
- drawing the serum into the syringe;
- lowering said syringe into an assay well and retracting said shield into said sheath so that said shield no longer covers the proximal end of the syringe;
- assaying said serum in the assay well;
- extending said shield over the proximal end of the syringe and withdrawing the syringe from the assay well; and
- injecting said serum into the patient.

* * * * *